United States Patent
Apostolov et al.

(10) Patent No.: US 7,052,909 B1
(45) Date of Patent: May 30, 2006

(54) METHOD FOR ACTIVATING NKT CELLS USING PIMS

(75) Inventors: Irina Apostolov, Paris (FR); Gabriel Gachelin, Paris (FR); Philippe Kourilsky, Paris (FR); Yousuke Takahama, Tokushima (JP)

(73) Assignees: Institut National de la Sante et de la Recherche Medicale, Paris (FR); Institut Pasteur, Paris (FR)

( * ) Notice: Subject to any disclaimer, the term of this patent is extended or adjusted under 35 U.S.C. 154(b) by 0 days.

(21) Appl. No.: 09/959,098

(22) PCT Filed: Apr. 19, 2000

(86) PCT No.: PCT/FR00/01029

§ 371 (c)(1),
(2), (4) Date: Jan. 18, 2002

(87) PCT Pub. No.: WO00/63348

PCT Pub. Date: Oct. 26, 2000

(30) Foreign Application Priority Data

Apr. 19, 1999 (FR) .................................. 99 04897

(51) Int. Cl.
*C12N 5/08* (2006.01)
*C12N 5/02* (2006.01)

(52) U.S. Cl. ........................ 435/372; 435/375; 435/383
(58) Field of Classification Search ................ 435/372, 435/375, 383
See application file for complete search history.

(56) References Cited

FOREIGN PATENT DOCUMENTS

| WO | WO 99/12562 | * 3/1999 |
| WO | WO 99/52547 | * 10/1999 |

OTHER PUBLICATIONS

Apostolou et al. PNAS, 1999, v.96, pp. 5141-5146.*
Gilleron et al., J of Biol. Chem. 2003, v.278, p 29880-29889.*
Apostolou, I. et al., "Murine Natural Killer Cells Contribute to the Granulomatous Reaction Caused by Mycobacterial Cell Walls", Proc. Natl. Acad. Sci. USA, vol. 96, pp. 5141-5146, (1999).
Kobayashi, E. et al., "Enhancing Effects of Agelasphin-11 on Natural Killer Cell Activities of Normal and Tumor-Bearing Mice", Bio. Pharm. Bul., vol. 19, No. 3, pp. 350-353, (1996).
Stankova, J. et al., "Fucose-Activated Killer (FAK) Cells: Anomalous Killers with Augmented Cytotoxic Activity", The Journal of Immunology, vol. 135, No. 6, pp. 3719-3728, (1985).
Kawano, T. et al., "Use of an Alpha-glycosyl-Ceramide of Formula (I) or Its Salt or Solvate as a Natural Killer (NK) T Cell Activator . . . ,", Derwent Publications Ltd., London, GB: Abstract of WO 98 44928 A1, (1 page), (1998).

* cited by examiner

*Primary Examiner*—Christina Chan
*Assistant Examiner*—Michail A. Belyavskyi
(74) *Attorney, Agent, or Firm*—Finnegan, Henderson, Farabow, Garrett & Dunner LLP

(57) ABSTRACT

The invention concerns a pharmaceutical composition comprising at least a PIM-activated NKT cell and the use of at least one PIM and/or a PIM-activated NKT cell for treating a disease for which a granulomatous type of immune response is desired.

3 Claims, 9 Drawing Sheets

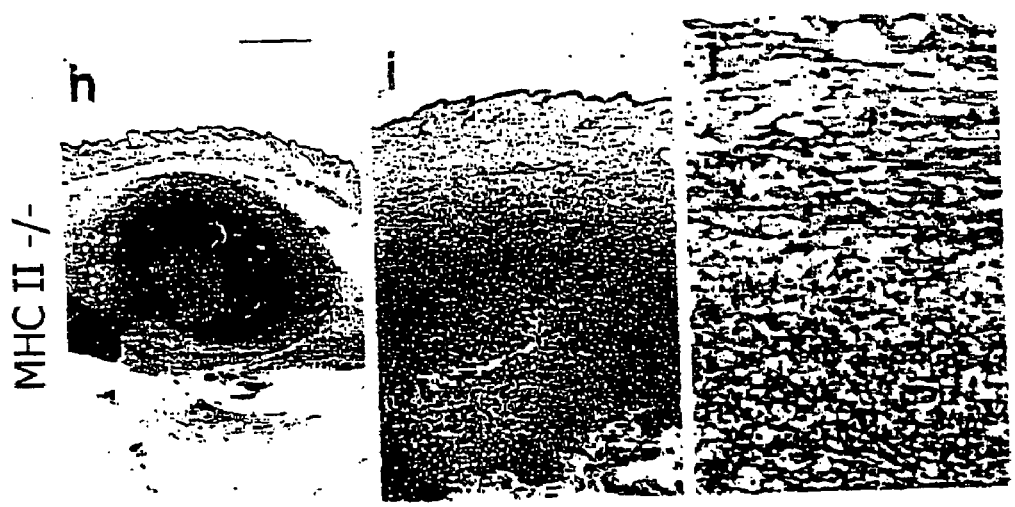
FIG.2A(end)

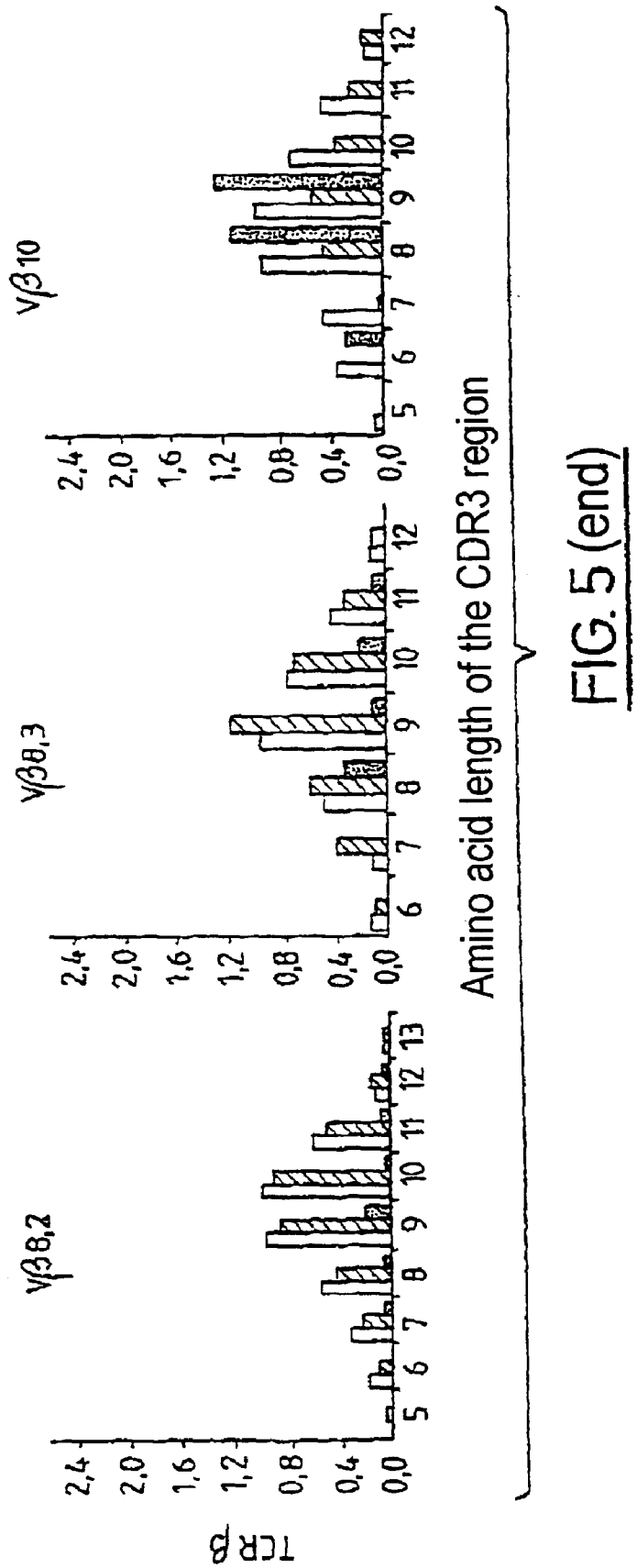
FIG. 5 (end)

SEQUENCE LISTING

<160> NUMBER OF SEQ ID NOS: 29

<210> SEQ ID NO 1
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcccatggaa ctgcacttgg c                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttgggtgga gtcacatttc tc                                             22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctaagcacag cacgctgcac a                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggcgttggt ctctttgaag                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acacagcagg ttctgggttc                                                20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggtatgac aatcagctga gtcc                                           24

<210> SEQ ID NO 7
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
cagctgagtc ccagctcc                                                        18

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)
<223> OTHER INFORMATION: a, c, t, g, unknown or other

<400> SEQUENCE: 8
gctgaacctc tatcncccac c                                                    21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgaattcgg cgcttgctgc tgc                                                  23

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacaagctta agtctgagag tcttcc                                               26

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgctgattcc ccttccttcc                                                      20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tagaatccta gcttgaccta ag                                                   22
```

```
<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggatccat atagacaacg aagg                                          24

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggataatcga ctcaccc                                                  17

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttctttccag ttaaagttg                                                19

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtaatgatca gtcaacgggg gac                                           23

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccagcaagct tgcaacctta acca                                          24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcctcagaag catgataagc                                               20

<210> SEQ ID NO 19
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cccagagtga tacagatgtc                                              20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttcagtgttg ttctggtag                                               19

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctggatccgg cacatgcaga tctc                                         24

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agtccttccc aaatgtcttc cc                                           22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
attcagaagg caacaatgaa ag                                           22

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctgtagtctt ccagaaatca c                                            21

<210> SEQ ID NO 25
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tttcaccaga caagcaaca                                                    19

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cggcaaaaaa caaatcaaca                                                   20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctataacttc gtcagttcca c                                                 21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cctcctaagg gtcgttgatt                                                   20

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cttgtccggg ccttcat                                                      17
```

METHOD FOR ACTIVATING NKT CELLS USING PIMS

The present invention relates to the use of at least one PIM and/or at least one PIM-activated NKT cell, for the treatment of a disease, for which an immune reaction of the granuloma-tous type is desired.

NKT cells are a specific subgroup of α/βT lymphocytes expressing cell surface markers associated with NK (Natural Killer) cells, such as NK1.1 (Bendelac et al., 1995) and certain members of the Ly-49 family (Ortaldo et al., 1998). They also differ from conventional T lymphocytes by several characteristics of their T receptors: the αchain is invariant and results from a rearrangement between the Vα14 and Jα281 segments associated with a conserved region of CDR3 (Koseki et al., 1991; Lantz et al., 1994). They also use a restricted TCRβ repertoire (Bendelac et al., 1997). Finally, and unlike conventional T cells, NKT cells express the TCR receptor (T cell receptor) at an intermediate level and are restricted by the class Ib MHC molecule CD1 (Bendelac et al., 1997). The α1 and α2 domains of the CD1d1 molecule have a hydrophobic binding site which is suited to the lipid nucleus of glycosylceramides (Brossay et al., 1998) and proteins anchored via a GPI (glycosylphosphatidylinositol), creating CD1-glycolipid complexes which are recognized by NKT cells (Brossay et al., 1998; Kawano et al., 1997; Burdin et al., 1998; Brossay et al., 1998, Schofield et al., 1999).

The functions of NKT cells, in vivo, are far from being fully described. These NKT cells play a role in IL-12-mediated tumor rejection (Takeda et al., 1996; Cui et al., 1997; Kawano et al., 1998). They are also involved in certain human and murine autoimmune diseases and infectious processes, even through the production of cytokines of the Th-1 or Th-2 type (Hammond et al., 1998; Flesch et al., 1997; Enomoto et al., 1997) or through a decrease in the number of these cells (Mieza et al., 1996; Wilson et al., 1998; Emoto et al., *Eur. J. Immunol.* 1997; Emoto et al., *Inf. & Imm.*, 1997).

The mechanisms which initiate the in vivo activation of NKT cells are also poorly understood. Activation of these cells with a ceramide, α-galactosylceramide, has been demonstrated (Kawano et al., 1998 and WO 98/44 928). A recent article by Schofield et al., 1999 reports, moreover, the results of the response of peripheral NKT cells to various GPIs (glycophosphatidylinositol) in vivo.

The authors of the present invention have discovered, firstly, that NKT cells can be activated with phosphoinositol mannosides (PIMs) and, secondly, that this activation causes an immune reaction of the granulomatous type.

The authors of the present invention have also demonstrated that the activation of the NKT cells responsible for the granulomatous response is independent of the CD1/TCR pathway and depends, in fact, on the pathway of CD14-mediated innate immunity. The NKT-cell-activating PIMs would make it possible to direct the host's response toward a pathway of the TH1 type. The inventors have been able to show this with direct measurement of the cytokines released within the granuloma.

On the basis of these results, the authors of the present invention propose to use at least one PIM and/or at least one PIM-activated NKT cell, for the treatment of a disease, for which an immune reaction of the granulomatous type is desired.

In accordance with the present invention, the phosphotidylinositol mannoside (PIM) may be used in combination with a pharmaceutically acceptable vehicle.

The phosphatidylinositol mannoside used may be obtained by chemical synthesis, for example from inositol phosphate, by reaction with a diacylglycerol then mannosylation, according to known methods. The PIMs used may also be obtained by purification from bacterial walls.

The PIMs can be purified from bacterial walls according to the standard techniques known to those skilled in the art. Preferably, the PIM used is of mycobacterial origin and may, for example, be obtained from *Mycobacterium tuberculosis*.

Among PIMs which may be used, mention may be made of those which correspond to the formula:

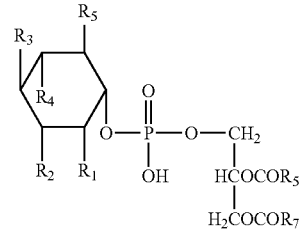

(I)

in which:

R$_1$, R$_2$, R$_3$, R$_4$ and R$_5$ are, independently of one another, selected from a hydroxyl group and a (Man)$_x$ group, in which (Man)$_x$ is at least one mannoside group linked to inositol, x being the number of mannose units (attached to one another in linear fashion), which preferably varies from 1 to 6;

R$_6$ or R$_7$ are, independently of one another, a fatty acid residue, preferably comprising from 18 to 24 carbon atoms, and preferably not comprising a double bond, and even more preferably not comprising a polar substituent.

Preferentially, R$_1$, R$_2$, R$_3$, R$_4$ and R$_5$ are such that only two of them, preferably adjacent to one another, are a (Man)$_x$ group, the other three groups then being a hydroxyl group.

Preferably, the PIMs used are the PIMs of formula (I) in which R$_2$ and R$_3$ are (Man)$_x$ groups and R$_1$, R$_4$ and R$_5$ are OH groups.

It is also possible to use, for example, PIMs of formula (I), in which:

R$_1$, R$_4$ and R$_5$ are OH groups;
R$_2$ is a mannoside group [(Man)$_x$ with x=1]; and
R$_3$ is (Man)$_x$ with x from 1 to 6.

It is also possible to use a PIM which is modified such that it contains not two but just one fatty acid residue.

In accordance with the present invention, the PIMs comprising 4, 5 or 6 mannose units are preferred.

The present invention also provides a pharmaceutical composition comprising at least one PIM-activated NKT cell, in combination with a pharmaceutically acceptable vehicle.

The authors of the present invention have discovered that PIM-activated NKT cells differ from ceramide-activated NKT cells, for example. The activation of NKT cells by a PIM is, in fact, thought to be relatively specific and to involve an oligoclonal distribution. On the other hand, the activation of NKT cells by a ceramide, for example, is thought to be polyclonal and is not thought to cause an intense granulomatous response.

In accordance with the present invention, the activation of NKT cells with a PIM can be carried out in vivo or ex vivo.

The present invention therefore also provides a method for activating NKT cells in vivo, comprising the steps consisting in:
i) administering at least one PIM, in combination with a pharmaceutically acceptable vehicle, to an individual;
ii) taking from said individual a biological sample containing NKT cells, such cells having been activated in vivo with said PIM.

The NKT cells activated with a PIM in vivo can then be administered to an individual requiring such treatment, who may be the individual from whom the biological sample was taken or another individual. Such a method in particular makes it possible to inject these activated NKT cells at a specific site of an individual at which a granulomatous response is desired.

The present invention also provides a method for activating NKT cells ex vivo, comprising the steps consisting in:
i) taking a biological sample containing NKT cells;
ii) bringing, the NKT cells into contact with at least one phosphatidylinositol mannoside (PIM), under suitable conditions for the PIM to activate the NKT cells.

The NKT cells activated with a PIM ex vivo can then be administered to an individual requiring such a treatment. Such a method in particular makes it possible to inject these activated NKT cells at a specific site of an individual at which a granulomatous response is desired.

The present invention therefore also provides a method for the therapeutic treatment of a condition, for which an immune reaction of the granulomatous type is desired, said method comprising the administration, to an individual who requires such a treatment, of a therapeutically effective amount of at least one PIM and/or of PIM-activated NKT cells.

The present invention also relates to the use of at least one phosphatidylinositol mannoside (PIM) and/or at least one PIM-activated NKT cell, for manufacturing a medicinal product intended for the treatment of a disease, for which an immune reaction of the granulomatous type is desired.

The term "treatment" is intended to mean any intervention for curative but not preventative therapeutic purposes.

Said disease may in particular be a disease of which the cause is an infection with bacterial agents, for example mycobacteria, such as the mycobacteria responsible for leprosy and for tuberculosis. The PIMs or the PIM-activated NKT cells act by stimulating local immunity, and in particular mucosal immunity, during a bacterial infection.

The modes of administration, the doses and the pharmaceutical forms of the pharmaceutical compositions according to the invention may be determined in the conventional way by those skilled in the art, in particular according to the criteria generally taken into account in establishing a therapeutic treatment suitable for a patient, such as for example the age or body weight of the patient, the seriousness of his or her general condition, the tolerance to the treatment, etc.

Advantageously, a pharmaceutical composition according to the invention, containing a PIM or PIM-activated NKT cells, may be administered intravenously or subcutaneously for example.

The medicinal product according to the invention may in particular be useful for the treatment of cancers, such as for example melanomas which are known to regress during intense granulomatous responses. In this case, the PIMs or the PIM-activated NKT cells may advantageously be used as adjuvants to known antitumor agents.

The following examples and figures illustrate the invention without limiting the scope of the invention.

LEGEND TO THE FIGURES

FIG. 1A represents hematoxylin/eosin-stained sections of a structure of the granulomatous type caused by injection of deproteinized mycobacterial cell walls. The equivalent of $10^6$ deproteinized mycobacterial cell walls were injected subcutaneously into C57BL/6 mice. On day 7 following the infection, the structures of the granulomatous type which developed were excized, fixed in 4% buffered formalin, covered with paraffin and sectioned. The objectives used are 2.5 (a), 6.3 (b) and 40 (c), respectively. The bar corresponds to 1 mm.

FIG. 1B represents the analysis by immunoscope of the Vα14-Cα (left-hand column) and Vα14-Jα281 (right-hand column) profiles observed seven days after the injection of PBS or of deproteinized mycobacterial cell walls into C57BL/6 mice:
a and b: lymph nodes of mice into which PBS was injected.
c and d: lymph nodes of mice immunized with deproteinized mycobacterial cell walls.
e and f: skin and muscle dissected at the site of injection of PBS in the control mice.
g and h: structure of the granulomatous type on day 7, caused by the injection of deproteinized mycobacterial cell walls.
i and j: cellular infiltration on day 3.
x-axis: length in amino acids of the CDR3 region.
y-axis: relative intensity of fluorescence.

FIG. 2 shows that the development of a structure of the granulomatous type which is relatively large in size depends on the recruitment of NKT cells.

Figure 3:
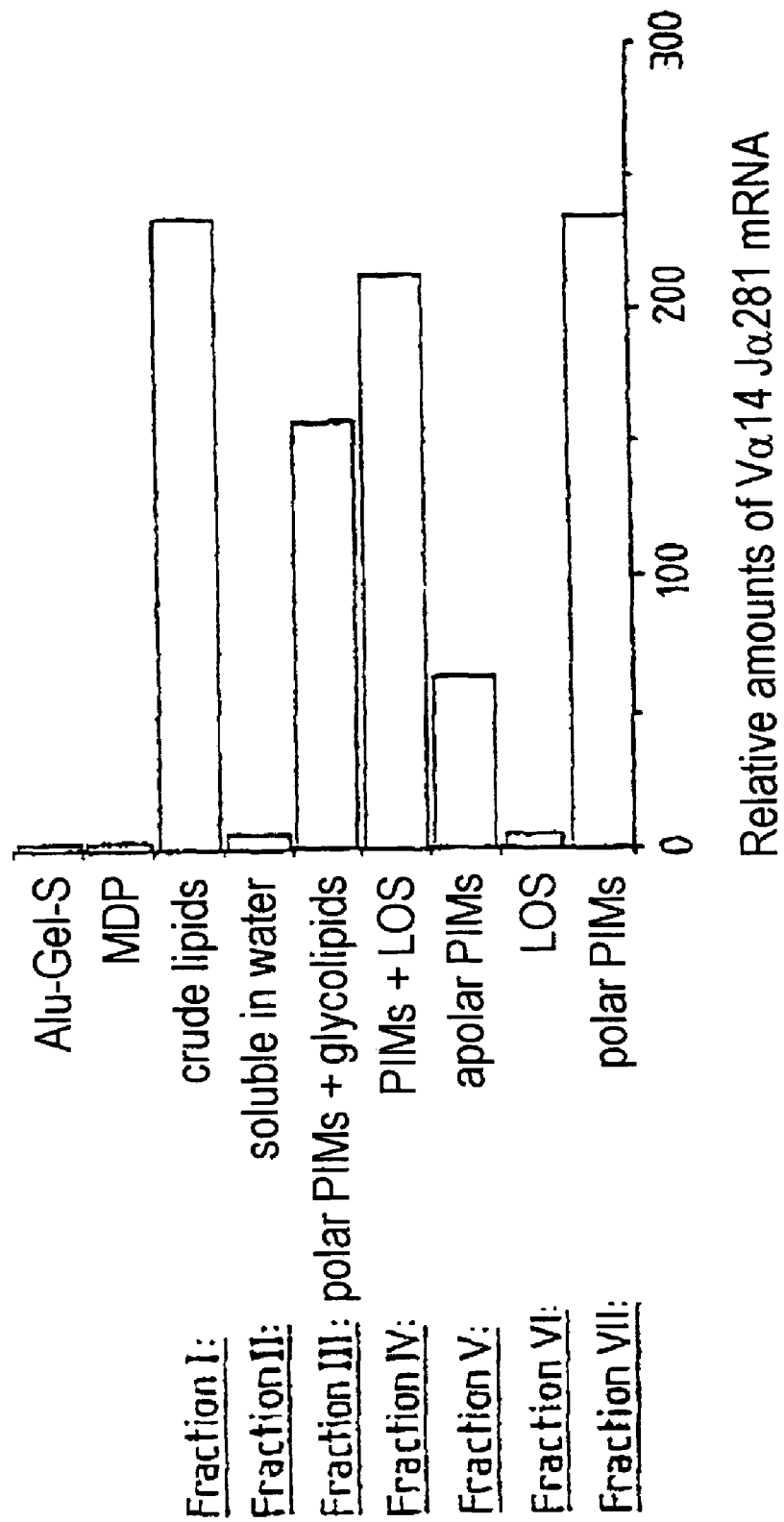

FIG. 3 represents relative amounts of Vα14 and Jα281 mRNA following immunization with Alu-Gel-S (aluminum hydroxide) (0.25 mg), MDP (40 μg), the crude mycobacterial lipids and fractions obtained therefrom. The material contained in approximately $10^6$ bacteria was injected after adsorption on Alu-Gel-S. The results (expressed as the fluorescent PCR using Vα14-Jα281 primers/fluorescent PCR signal using hypoxanthine ribosyltransferase (HPRT) primers ratio) correspond to the mean of the results obtained in two animals.

Figure 4:
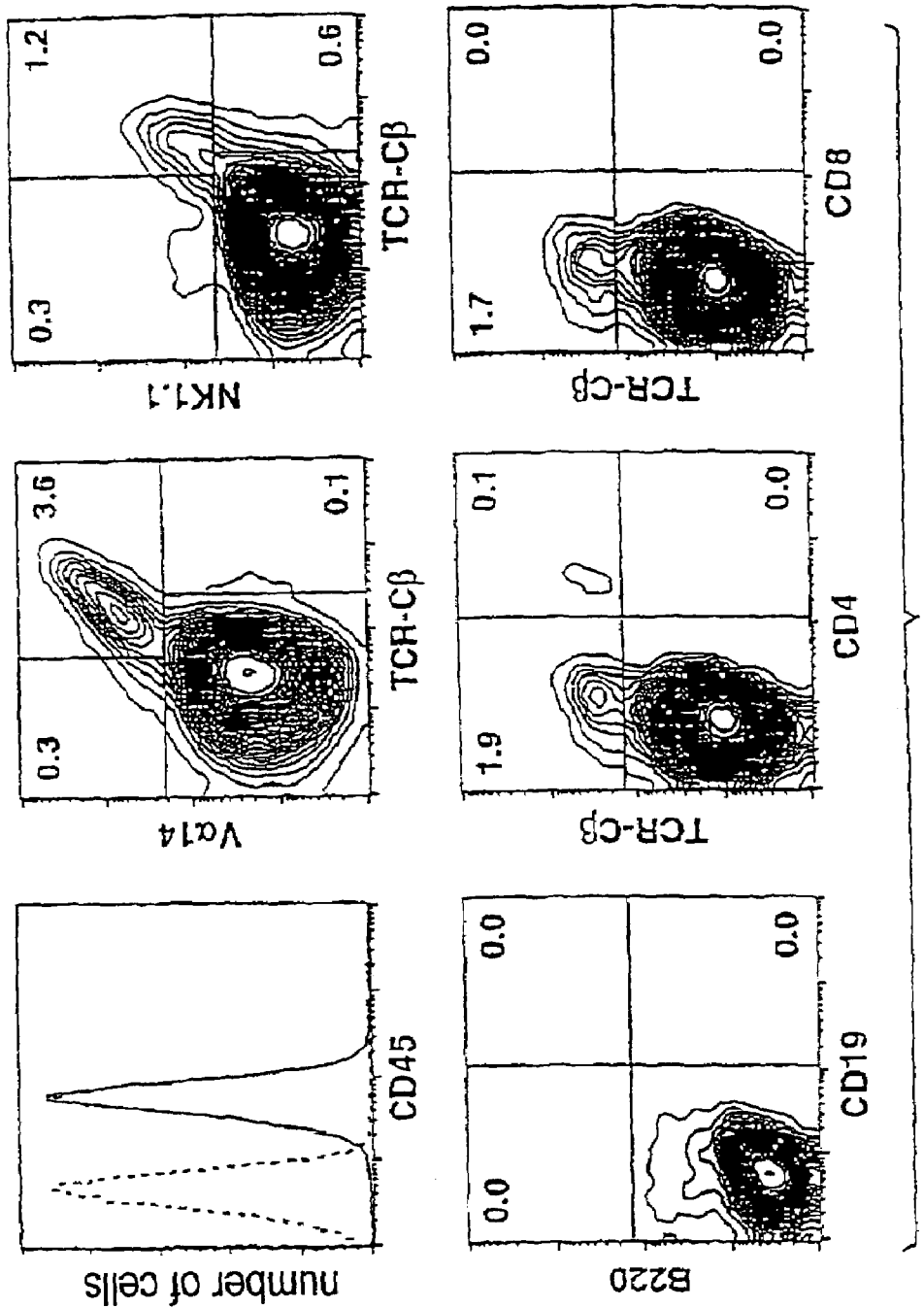

FIG. 4 represents the FACS analysis of the cells harvested at the site of subcutaneous injection of Alu-Gel-S/mycobacterial lipids into C57BL/6 mice. According to the experiments, the frequency of NKT cells ranges from 1.7 to 3.6% of the total cells harvested, after Ficoll fractionation. The broken line on the histogram corresponds to the unstained cells.

Figure 5:
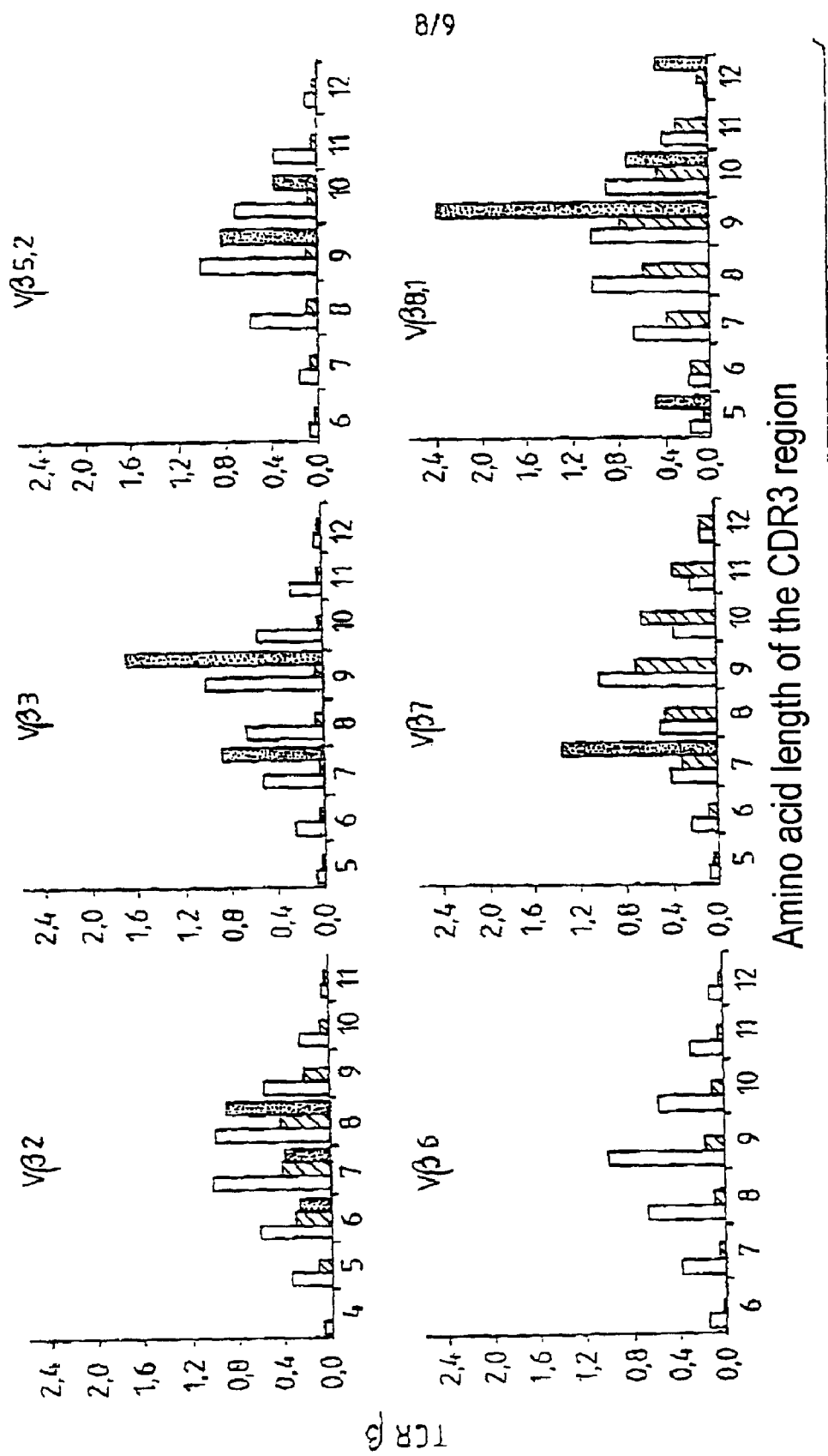

FIG. 5 represents the semiquantitative analysis of the TCRβ chain repertoire of the NKT cells isolated from the liver of control mice (hatched columns) and recruited with $PIMs_{4-6}$ (columns with scattered dots) and of T cells from lymph nodes used here as an internal control for the effectiveness of the primers (clear columns): the value 1 is attributed arbitrarily to the area of the highest peak of the gaussien profile obtained using the T cells from the lymph node. Only the most represented Vβ-Cβ families in the structures of the granulomatous type were studied by semi-quantitative PCR analysis. Vβ6, which is absent from structures of the granulomatous type, was used as a negative control.

EXAMPLES

Materials and Methods

Animals

The animals used are: C57BL/6 mice; C57BL/6 class II MHC−/− mice (Cosgrove et al., 1991); C57BL/6 β2m−/− (Koller et al., 1990); Jα281−/− (Cui et al., 1997) and Jα281+/− mice were backcrossed 9 and 6 times, respectively, using 129/Sv− in the C57BL/6 genetic background, at the time of experiments.

Bacterial strains and extracts:

*Mycobacterium tuberculosis* bacteria (H37Rv strain) were cultured on a semisolid medium and were then killed with heat (75° C., 30 minutes). After sonication in $10^{-2}$M Tris, pH 8.0, $10^{-3}$M MgCl$_2$, $10^{-3}$M CaCl$_2$ and $1.5 \times 10^{-1}$M NaCl, the mycobacteria were digested for 5 hours at 37° C. with 25 mg/ml of DNase and of RNAse. The digestion was followed by heat inactivation. After several washes, the preparation was incubated for 24 hours at 37° C. with a mixture of trypsin, chymotrypsin and subtilisin (Boehringer) at a final concentration of 200 μg/ml for each enzyme, in the same buffer as described above, to which 0.5% of SDS is added. The enzymes were heat-inactivated (10 minutes at 70° C.). The resulting particles were washed and resuspended in phosphate buffer (PBS). The absence of proteins in the suspension was then determined by PAGE electrophoresis and amino acid analysis. Samples were standardized on the basis of their sugar content.

The mycobacterial lipids were extracted and fractionated as follows: 4 g of heat-killed *M. tuberculosis* H37Rv bacilli were extracted twice with CHCl$_3$/CH$_3$OH (1:1, v/v). The extracts were dried, resuspended in CHCl$_3$/H$_2$O and left for one hour at 4° C. in order for an organic phase of crude lipids (fraction I) to separate out from an aqueous phase (including the interface: LAMs, polysaccharides and denatured proteins) (fraction II). Fraction I is free of phosphoantigens for γ/δ T cells in humans (Constant et al., 1994), but comprises several glycolipid components. This fraction was dried and separated once more by precipitation in cold acetone (10° C.) so as to give a soluble extract (fat, phenolic glycolipids) and an insoluble white precipitate. Hot acetone (50–60° C.) was added to the waxy pellet, which made it possible to resuspend the antigens of mycolic acid substituted with a trehalose, and other glycolipids (fraction III), and to precipitate all of the PIMs and lipooligosaccharides (LOS's) (fraction IV). Fraction IV was dried and separated by solubilization with methanol so as to give PIMs (white pellet, fraction V) and soluble LOS's (fraction VI). In cooling fraction III, some polar PIMs precipitate and give fraction VII. All the fractions were analyzed by thin layer chromatography (TLC) on silicic acid pF254 (Merck) eluted with CHCl$_3$/CH$_3$OH/H$_2$O, 60/35/5, and using an *M. tuberculosis* PIM2 as a standard, the spots being revealed using an anthrone/sulfuric acid spray.

PCR primers:

The specific Vβ primers, with the exception of Vβ8.2 (Regnault et al., 1996), were described in Pannetier et al., 1993. The unlabeled specific Cβ primer used for the PCR is GCCCATGGAACTGCACTTGGC (SEQ ID NO: 1). The labeled specific Cβ primer is FAM-CTTGGGTGGAGTCA-CATTTCTC (SEQ ID NO: 2). Regarding the mRNA of the Vα14 chains, the following primers were used: the Vα14 primer was CTAAGCACAGCACGCTGCACA (SEQ ID NO: 3); the unlabeled Cα primer was TGGCGTTG-GTCTCTTTGAAG (SEQ ID NO: 4). The labeled specific Cα primer was FAM-ACACAGCAGGTTCTGGGTTC (SEQ ID NO: 5). The unlabeled specific Jα281 primer was CAGGTATGACAATCAGCTGAGTCC (SEQ ID NO: 6). The labeled specific Jα281 primer was FAM-CAGCT-GAGTCCCAGCTCC (SEQ ID NO: 7). The labeled specific clonotypic primer was FAM-GCTGAACCTCTATCNC-CCACC (SEQ ID NO: 8). The primers for CD4 were the 5' primer CTGAATTCGGCGCTTGCTGCTGC (SEQ ID NO: 9), the 3' primer CACAAGCTTAAGTCTGAGAGTCTTCC (SEQ ID NO: 10) and FAM-TGCTGATTCCCCTTCCT-TCC (SEQ ID NO: 11). The specific CD8 primers were: the 5' primer TAGAATCCTAGCTTGACCTAAG (SEQ ID NO: 12), the 3' primer ATGGATCCATATAGACAACGAAGG (SEQ ID NO: 13) and FAM-GGATAATCGACTCACCC (SEQ ID NO: 14). The primers for HPRT were FAM-TTCTTTCCAGTTAAAGTTG (SEQ ID NO: 15), the 5' primer GTAATGATCAGTCAACGGGGGAC (SEQ ID NO: 16) and 3' primer CCAGCAAGCTTGCAACCT-TAACCA (SEQ ID NO: 17). The primers for CD3ε were: the 5' primer GCCTCAGAAGCATGATAAGC (SEQ ID NO: 18) and 3'-FAM-CCCAGAGTGATACAGATGTC (SEQ ID NO: 19). The primers for the IgM heavy chains were: FAM-TTCAGTGTTGTTCTGGTAG (SEQ ID NO: 20), the 3' primer CTGGATCCGGCACATGCAGATCTC (SEQ ID NO: 21) and the 5' primer AGTCCTTCCCAAAT-GTCTTCCC (SEQ ID NO: 22). The unlabeled specific Vγ1, Cγ, Vδ2, Vδ4, Vδ5, Vδ6 and Cδ primers were described in Azuara et al., 1997. The Vδ1- and Vδ6P-specific primers were ATTCAGAAGGCAACAATGAAAG (SEQ ID NO: 23) and CTGTAGTCTTCCAGAAATCAC (SEQ ID NO: 24), respectively. The labeled specific Cδ primer was FAM-TTTCACCAGACAAGCAACA (SEQ ID NO: 25). The Vγ2- and Vγ7-specific primers were CGGCAAAAAA-CAAATCAACA (SEQ ID NO: 26) and CTATAACTTCGT-CAGTTCCAC (SEQ ID NO: 27), respectively. The labeled Vγ primer specific for the Vγ1 and Vγ2 segments was FAM-CCTCCTAAGGGTCGTTGATT (SEQ ID NO: 28) and the labeled Vγ7-specific primer was FAM-CTTGTC-CGGGCCTTCAT (SEQ ID NO: 29).

Semi-automated analysis of the T lymphocytes diversity ("immunoscope"):

The PCR-based technique used by the authors of the present invention is described in Pannetier et al., 1997; Cibotti et al., 1994; Levraud et al., 1996. Briefly, the total RNA is extracted from the samples and 10 μg of total RNA undergo reverse transcription using AMV (avian myeloblastosis virus) reverse transcriptase. The resulting cDNA is resuspended in a final volume of 100 μl.

The quality and the amount of the cDNA were controlled by assaying the HPRT mRNA. 1 μl was amplified via 40 PCR cycles (94° C., 1 min; 60° C., 1 min; 72° C., 4 min) using either specific Vα14 and Cα primers or each of the specific Vβ and Cβ primers. 2 μl of the PCR products were used in primer extensions (5 cycles) using fluorescent primers specific for the Jα281 or Cα segments. The length of the CDR3 region and the intensity of the fluorescence of each extension product family were determined using an automatic sequencer (Applied Biosystems). The size distribution for the CDR3 region of each V-C pair is described as a family of peaks separated by 3 nucleotides (derived from the in-frame mRNA), the area of which is proportional to the intensity of the fluorescence and therefore to the initial amount of cDNA. In the absence of a specific antigenic stimulation, 6 to 8 peaks with a gaussian-type distribution were observed. On the other hand, an antigen-induced T-lymphocyte response typically results in a non-gaussian distribution of the peaks, due to selective proliferation of the cells bearing certain particular V-C combinations. A semi-quantitative PCR was carried out using a procedure adapted from that described in Azuara et al., 1997, and with standardization based on the CD3ε mRNA. 10 000 murine T lymphocytes were sufficient to carry out a semiquantitative PCR analysis of the complete Vβ-Cβ repertoire using the immunoscope technique.

Antibodies and FACS analysis:

Cells: Granuloma cells were prepared by passing ground granulomas through a nylon cell filter (70 μm) (Becton-Dickinson strainer) and were washed once in phosphate buffer (PBS). The live cells were separated by Ficoll (Lymphocyte-M, Cedar Lane, Hornby, Ontario) fractionation. The liver leukocytes were obtained by discontinuous Percoll gradient.

Antibodies: The biotinylated anti-Vα14 antibody clone CMS-5 has been described previously (Masuda et al., 1997). The following antibodies were purchased from Pharmingen (San Diego, Calif.): PE-NK.1 (clone PK136), or biotinylated TCRβ (clone H 57-597), FITC-CD4 (clone RM4-5), FITC-CD44 (clone IM7), biotinylated CD45.2 (clone 104), PE-B220 (clone RA3-6B2), FITC-CD19 (clone 1D3) and FITC-CD8 (clone CT-CD8a). The FITC-CD8 antibody (clone CT-CD8a) was obtained from CALTAG (San Francisco, Calif.). The PE-streptavidin was obtained from Pharmingen and the APC-streptavidin was obtained from Molecular probes. The biotinylated, FITC-, and PE-(phycoerythrin) Igs from normal mice, used as negative controls, were purchased from Pharmingen.

FACS analysis: Before staining with specific antibodies, the cells were incubated with murine serum in order to block the nonspecific staining. Diverse antibody combinations were then added. The dead cells were discarded using propidium iodide staining. The lymphoid cells were selected on FCS and SSC. A minimum of 100 000 events was counted in the lymphocyte window. A four-color analysis was performed using a FACS-Vantage (Becton-Dickinson), and a three-color analysis was carried out using a FACS-Scan (Becton-Dickinson) The data were produced using the Cell-Quest program (Becton-Dickinson). The NKT cells from liver were sorted after labeling with anti-NK1.1 and anti-TcRβ antibodies, using a Becton-Dickinson FACStar$^+$ cell sorter.

Results

1. Injection of deproteinized mycobacterial cell walls results in the formation of lesions of the granulomatous type.

The authors of the present invention first of all examined whether murine NKT cells could be detected at the site of injection of deproteinized mycobacterial cell walls, which are rich in glycolipids.

Figure 1A:
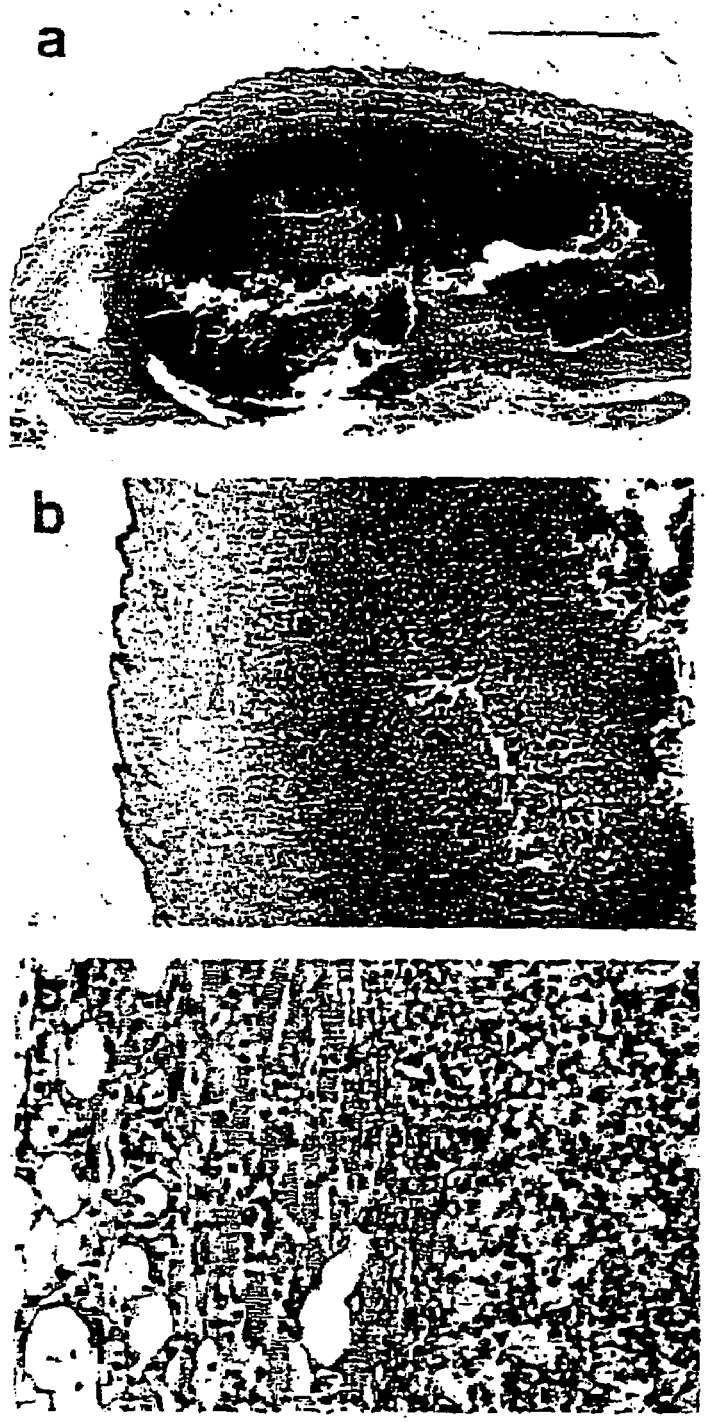

To this end, the suspension of deproteinized mycobacterial cell walls in PBS, equivalent to approximately $10^6$ *Mycobacterium tuberculosis* strain H37Rv virulent bacteria, was injected subcutaneously into the base of the tail of C57BL/6 mice. The animals into which PBS was injected were sacrificed on days 1, 2, 3 and 7 following immunization and no sign of an inflammatory process could be observed at the site of injection of the PBS. In the immunized mice, neutrophiles were observed, in a predominant manner, on smears prepared from cellular infiltrates harvested on days 1 and 2. Lymphocytes and macrophages were detected on day 3 and lesions adhering to the skin and to the muscles subsequently developed. They increased in size with time, reaching a diameter of 4–6 mm on day 7. A histological analysis was performed on the induced lesions on day 7. Stained sections revealed lesions of the granulomatous type, with a neutrophile-rich core surrounded by a border consisting of a dense row of macrophages, lymphocytes and fibroblasts (FIG. 1A).

2. NKT cells are the only Vα14+T cells which infiltrate granulomatous lesions.

Figure 1B:
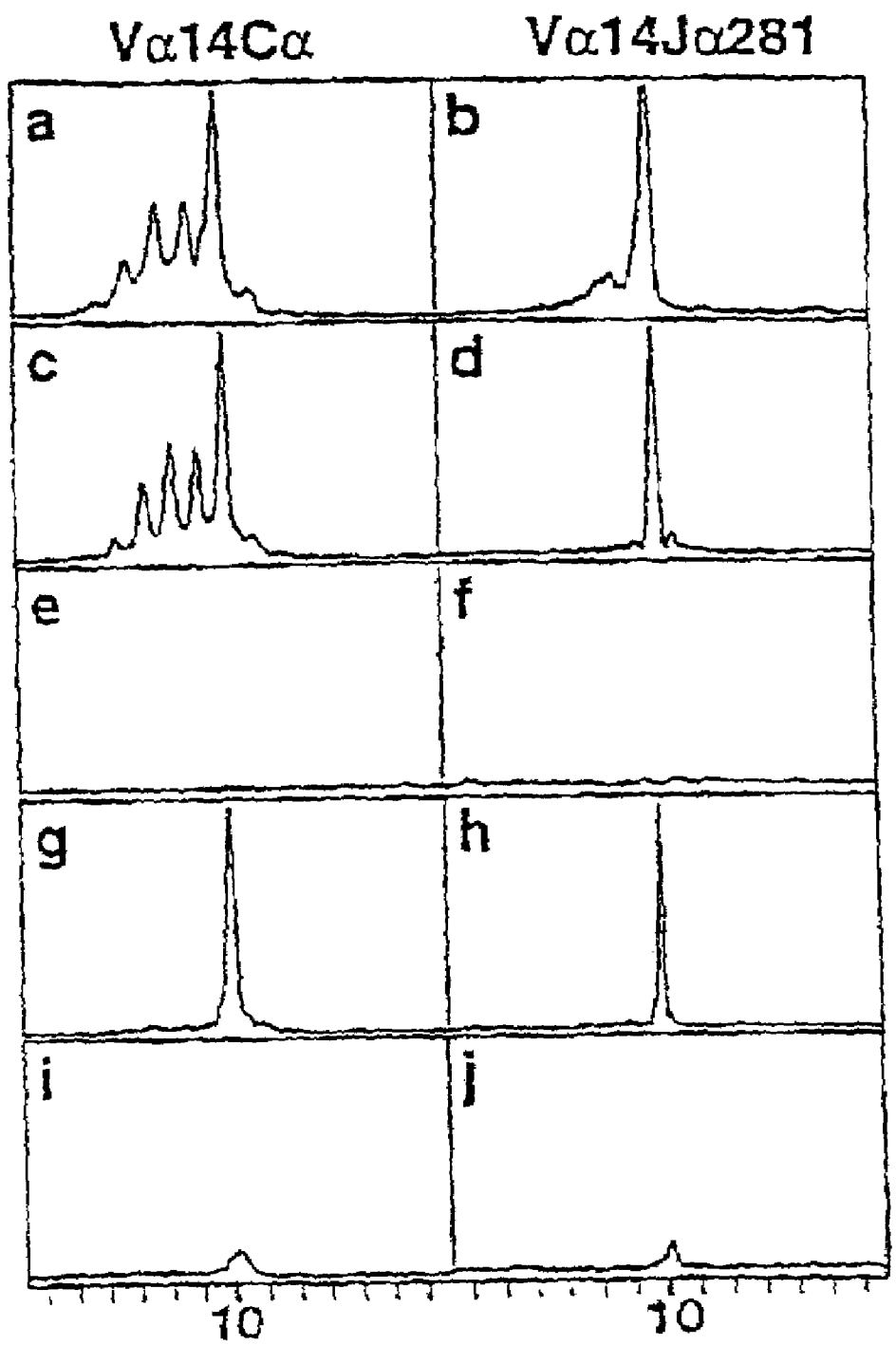

The structures of the granulomatous type on day 7 could not be dissociated into suspensions of live single cells, whether manually or by enzymatic digestion, which prevented a FACS analysis. A technique based on an RT-PCR (Immunoscope®) was used instead, in order to search for the mRNAs encoding markers specific for NKT cells. Since an almost invariant Vα14-Jα281 TCR chain, with a CDR3 10 amino acids in length, is the signature of murine NKT cells (Lantz et al., 1994), the cDNAs encoding Vα14, prepared from control and experimental samples, were amplified by PCR and analyzed for CDR3 size diversity by primer extension using either primers specific for Cα or primers specific for Jα281. The specific Cα primers produced signals representative of the diversity of the Vα14+α-chains of the samples. Several peaks were detected in the lymph nodes draining the site of injection in the control and immunized mice (FIG. 1B, a and c). The overall gaussian distribution of CDR3 size was modified by a predominant peak corresponding to a CDR3 length of 10 amino acids and containing Vα14-Jα281 rearranged TRC α-chains (FIG. 1B, b and d), thus including the NKT cells. No signal was detected in the skin and muscles dissected at the site of injection of PBS (FIG. 1B, e and f). On the other hand, the cDNAs encoding Vα14, prepared from the structures of the granulomatous type on day 7, produced a single peak with a CDR3 size of 10 amino acids, using either the specific Jα primers or the specific Cα primers (FIG. 1B, g and h). The direct sequencing of the Vα14-Cα PCR products, carried out on these lesions, made it possible to identify the TCR α-chains specific for NKT cells. The four nucleotide substitutions affecting codon 31 account for the diversity of the Vα14-Jα281 chains present in the infiltrating T cells. Thus, unlike the cells of the lymph nodes, which contain many conventional Vα14$^+$ T cells, all the Vα4$^+$ cells recruited into the structures of the granulomatous type on day 7 are NKT cells. A single Vα14-Cα peak with a CDR3 10 amino acids in length and containing the Jα281 segment was detected on day 3 following injection (FIG. 1B, i and j) and was then identified as being specific for NKT cells, using a clonotypic probe.

Consequently, the NKT cells are recruited at the earliest stages of the cellular infiltration due to the injection of deproteinized mycobacterial cell walls, and represent the only Vα14 T cells present in the lesions on day 7.

The use of the same RT-PCR technique enabled the authors of the present invention to detect the rearranged β-chains using the Vβ8.1, 7, 3, 5.2 and 10 segments. Conventional α/β CD4$^+$ T cells can only rarely infiltrate the lesions of the granulomatous type, since no mRNA encoding CD8 and little mRNA coding CD4 could be detected using the suitable primers. Finally, the results of the PCR analysis using primers specific for Igμs and for TCR γ/δ indicate the presence of significant numbers of B cells and of γ/δ T cells using, in particular, the Vδ5 and Vδ6 segments.

3. Involvement of α/β T cells in the granulomatous response to deproteinized mycobacterial cell walls Granulomatous responses are the result of multicellular processes containing several steps. In order to evaluate the possible involvement of α/β T cells in the granulomatous process, the authors of the present invention immunized mice genetically deficient for several T-cell subgroups.

Figure 2A:
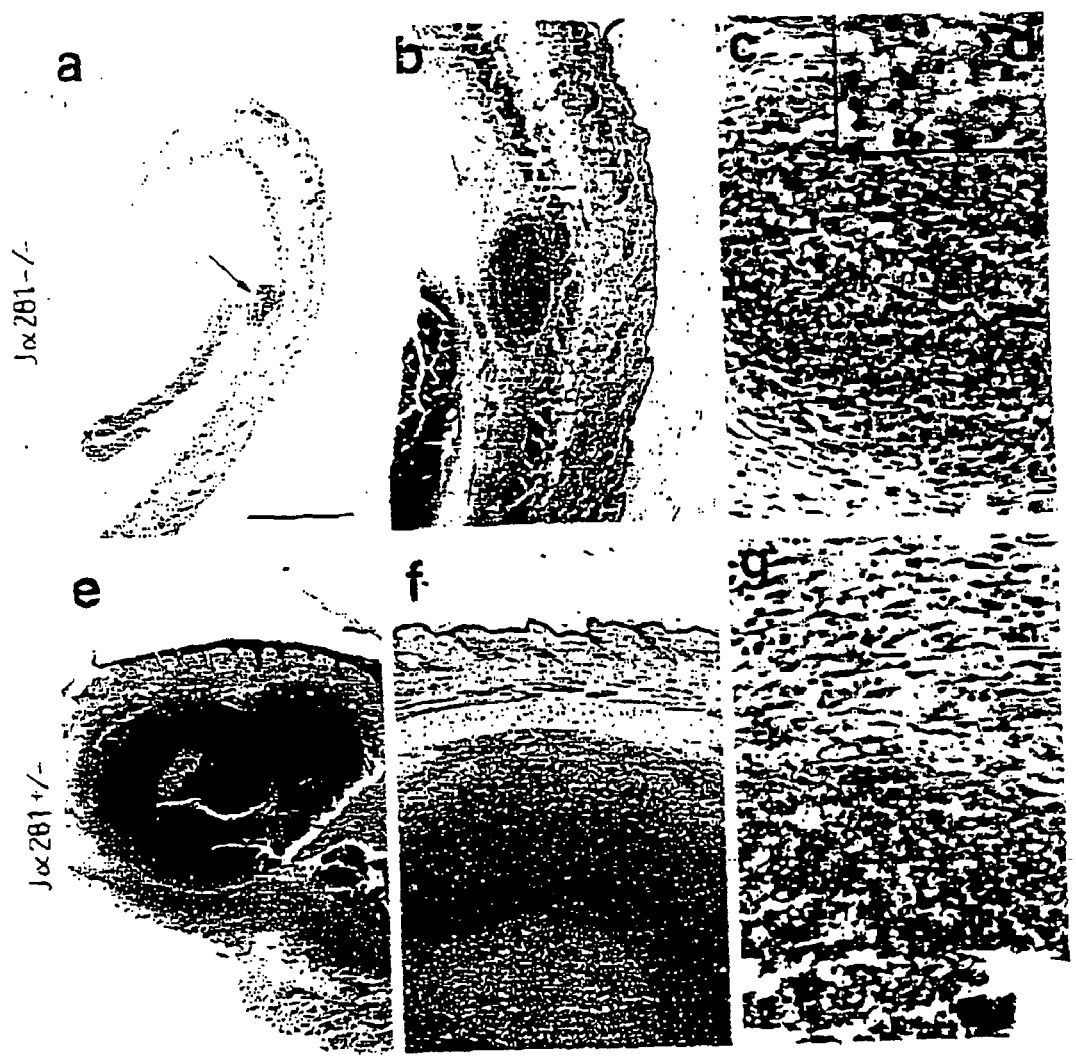
FIG. 2A represents stained sections of the site of injection, 7 days after the injection of deproteinized cell walls into Jα281−/− (objectives: a, 2.5; b, 6.3; c, 40 and d, oil, 100), Jα281+/− (e, 2.5; f, 6.3 and g, 40) and C57BL/6 class II MHC−/− (h, 2.5; i, 6.3 and j, 40) mice. The bar corresponds to 1 mm.
Figure 2B:
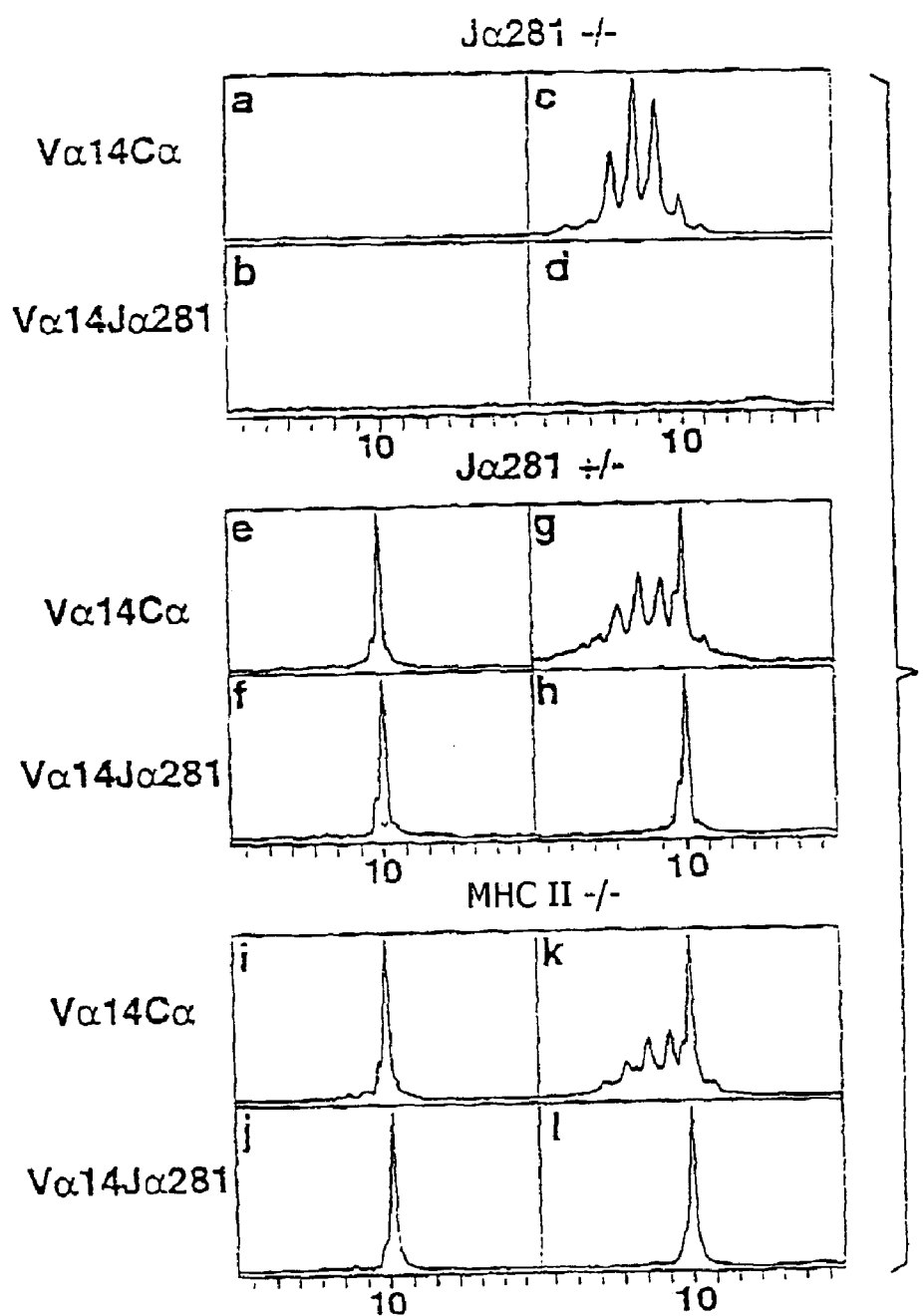
FIG. 2B represents Vα14 and Vα14-Jα281 use at the site of injection (left-hand columns) and in the lymph nodes (right-hand columns) of Jα281−/− (a to d), Jα281+/− (e to h) and C57BL/6 class II MHC−/− (i to l). The y-axes are identical to those of FIG. 1.

Jα281−/− mice (Cui et al., 1997) deficient for NKT cells, but in which conventional T cells and NK cells develop normally, were injected with deproteinized mycobacterial cell walls. In 5 out of 7 of the mice which received the injection, no lesions of the granulomatous type, but rather a small flattened infiltrate, was observed at the site of the injection. In the other two mice, a minute structured cellular infiltrate almost exclusively composed of macrophages developed (FIG. 2A, a to d). In none of the infiltrates was any mRNA encoding Vα14 (FIG. 2B, a and b) or any VβCβ rearrangement found. A Vα14-Cα gaussian profile was obtained from the lymph nodes in the immunized Jα281−/− mice, indicating normal use of the Vα14 segment by the conventional T cells in the absence of NKT cells (FIG. 2B, c and d).

According to the RT-PCR analysis, no μ-chain was detected and rearranged TCR γ-chains were found. As a control, the six Jα281+/− mice, which were injected with deproteinized mycobacterial cell walls, gave the same results as the C57BL/6+/+ mice (FIG. 2A, e to g; FIG. 2B, e to h). The formation of a fairly large lesion of the granulomatous type therefore requires the presence of NKT cells.

The authors of the present invention then examined the possible involvement of conventional CD4+ T cells. In MHC II−/− mice which are deficient for conventional CD4+ T cells, but in which the NKT cells differentiate normally, the injection of deproteinized mycobacterial cell walls led to the development of lesions of the granulomatous type, as in the C57BL/6+/+ animals (FIG. 2A, h to j). According to the immunoscope analysis of the samples, the Vα14-Jα281 invariant TCR α-chain was the only Vα14 chain detected (FIG. 2B, i and j). The Vα14-Cα and Vα14-Jα281 profiles in the lymph nodes of the class II −/− mice are the same as in the C57BL6+/+ animals (FIG. 2B, k and l). In addition, the TCRβ repertoire of the cells present in the lesions, on day 7, of the MHC II −/− cells showed the same bias in Vβ use as in the C57BL/6+/+ mice. In addition, the mRNAs encoding the Ig μ-chain and the TCR γ/δ-chains were detected as in the C57BL6+/+ mice.

Thus, the diverse cell types present in the lesions of the granulomatous type induced by mycobacterial cell walls assemble into a highly organized structure in the absence of CD4+ T cells but do not become organized in the absence of NKT cells.

The absence of mRNA encoding CD8 excludes a predominant role for conventional CD8+ T cells. The role of CD1 molecules in the granulomatous process was evaluated using β2m−/− mice, which lack CD1-dependent NKT cells. Large lesions of the granulomatous type developed. However, their lymphocyte content was markedly different from that observed in the structures of the granulomatous type induced in the C57BL/6+/+ mice: according to the RT-PCRs and the immunoscope analysis, the mRNAs encoding the TCR β-chains and TCR Vα14+-chains, CD4, CD8 and the IgM μ-chains were not detectable. On the other hand, the mRNAs encoding the γ/δ-chains of the TCR were present as in the C57BL6+/+ mice.

The phenotypic changes due to the modification of the β2m gene therefore prevent the accumulation of B lymphocytes and of α/β T cells in the lesions caused by deproteinized mycobacterial cell walls, and also prevent the accumulation, in the lesion, of rare NKT cells, which are detected in the lymph nodes of the same animals using a clonotypic probe.

4. The activity of NKT-cell recruitment is associated with glycobacterial glycolipids, more particularly with PIMs.

In order to identify the nonpeptide mycobacterial components responsible for the accumulation of NKT cells, the material was fractionated and the activity of NKT-cell recruitment of the various fractions was evaluated in vivo. The relative amounts of NKT cells present on day 7 at the site of injection were determined by RT-PCR and Immunoscope analysis. In order to avoid possible differences in the in vivo behavior of the molecules injected (for example, differences in the diffusion rate or the specific internalization process), the material injected was conjugated to a neutral vehicle, aluminum hydroxide (Alu-Gel-S, Serva). The C57BL6+/+ mice which were injected subcutaneously with Alu-Gel-S in the form of particles of 0.25 mg developed a weak infiltrate with a barely detectable Vα14-Jα281 mRNA (FIG. 3).

The crude lipids of the H37Rv cellular fractions (fraction 1), adsorbed onto the Alu-Gel-S, caused large organized cell infiltrates with a core made up of the vehicle and neutrophiles, surrounded by a thick border of macrophages and lymphocytes. The formation of these structures also proved to depend on the presence of NKT cells, since they do not form in the Jα281−/− mice. However, and unlike the structures induced by the deproteinized cell walls, the organized cell infiltrates induced by the crude glycolipids could be dissociated into single live cells, thus allowing the direct identification of NKT cells in the infiltrates, by FACS analysis. The dead cells and the macrophages were removed by Ficoll fractionation. Most of the $2 \times 10^6$ live cells which were harvested from each granuloma were identified as being neutrophils. FIG. 4 shows that all the other cells were CD45+leukocytes. No CD19+B220+B cell was found. All the α/β T lymphocytes were Vα14+, TCR pint (intermediate expression) and NK1.1+, i.e. NK1.1+ T cells. No CD8+ cell was detected and CD4+ cells were rarely detected. Approximately 0.3% were non-T NK cells and approximately 0.1% were γ/δ T cells. The RT-PCR and Immunoscope analyses confirmed the absence of B cells and the presence of rearranged TCR γ/δ-chains in the infiltrates caused by the injection of fraction I. Almost all the T cells infiltrating the lesions caused by the crude lipids were therefore CD4− CD8− NKT cells. The infiltrate induced by fraction I turned out, by RT-PCR analysis, to contain up to 200 times more Vα14-Jα281 RNA than the cells recruited at the site of injection of Alu-Gel-S (FIG. 3). Although it is capable of activating γ/δ T cells in humans (Constant et al., 1994), the nonlipid fraction (fraction II) was ineffective in recruiting NKT cells (FIG. 3). The immunoadjuvant muramyl-dipeptide (MDP, Sigma), a component of mycobacterial cell walls, produced a cellular infiltrate without increasing the Vα14-Jα281 mRNA in comparison with the Alu-Gel-S alone (FIG. 3). Fraction I was fractionated and the activity of NKT cell recruitment of the fractions was monitored by RT-PCR. Almost all the activity was detected in the fractions containing PIMs (fractions II, IV, V and VII) (FIG. 3) and the area of the Vα14-Jα281 peak was proportional to the amount of material injected. According to the analysis of the reactive fractions by TLC using "FLASH LC®" (Merck) with a "Kieselgel G60 silicagel", the fractions most active in recruiting NKT cells were those containing highly polar PIMs, the structure of which, by mass spectrometry analysis, is compatible with PIMs comprising 4 to 6 mannose units.

In order to determine whether the NKT cells accumulate randomly in the infiltrates induced by the PIMs 4–6, an Immunoscope-derived semiquantitative PCR technique was used to define their TCRβ repertoire and compare it to the repertoire of NKT cells from liver chosen arbitrarily to represent peripheral NKT cells (Watanabe et al., 1995) (FIG. 5). It was confirmed that the NKT cells from liver had a Vβ use restricted toward Vβ8 and Vβ7 in comparison with conventional T cells. Each Vβ-Cβ rearrangement family showed a gaussian distribution for CDR3 length, indicating a polyclonal and diversified TCRβ repertoire.

On the other hand, the NKT cells present in the infiltrate caused by the injection of PIMs 4–6 showed a Vβ use limited differently (FIG. 5). In addition, the rearrangements associated with a given CDR3 length (such as Vβ8.1-Cβ rearrangements with a CDR3 length of 9 amino acids, as in FIG. 5) and found in large excess in comparison with the gaussian distribution observed in the controls, revealed an oligoclonal distribution of the NKT cells in the infiltrates. The same limitation in Vβ use, associated with oligoclonal distributions, was observed in all the mice studied, but the length of the CDR3 regions varied depending on the animals.

BIBLIOGRAPHY

Bendelac, A., Lantz, O., Quimby, M. E., Yewdell, J. W., Bennink, J. R. & Brutkiewicz, R. R. (1995) *Science* 268, 863–865.

Bendelac, A., Rivera, M. N., Park, S. H. & Roark, J. H. (1997) *Ann. Rev. Immunol.* 15, 535–562.

Brossay, L., Chioda, M., Burdin, N., Koezuka, Y., Casorati, G., Dellabona, P. & Kronenberg, M. (1998) *J. Exp. Med.* 188, 1521–1528.

Brossay, L., Naidenko, O., Burdin N., Matsuda, J., Sakai, T. and Kronenberg, M. (1998) *J. Immunol.* 161, 5124–5128.

Burdin, N., Brossay, L., Koezuka, Y., Smiley, S. T., Grusby, M. J., Gui, M., Taniguchi, M., Hayakawa, K. & Kronenberg, M. (1998) *J. Immunol.* 161, 3271–3281.

Cibotti, R., Cabaniols, J. P., Pannetier, C., Delarbre, C., Vergnon, I., Kanellopoulos, J. M. & Kourilsky, P. (1994) *J. Exp. Med.* 180, 861–872.

Constant, P., Davodeau, F., Peyrat, M.-A., Poquet, Y., Puzo, G., Bonneville, M. & Fournier, a. J.-J. (1994) *Science* 264, 267–270.

Cosgrove, D., Gray, D., Dierich, A., Kaufman, J., Lemeur, M., Benoist, C. & Mathis, D. (1991) *Cell* 66, 1051–1066.

Cui, J., Shin, T., Kawano, T., Sato, H., Kondo, E., Toura, I., Kaneko, Y., Koseki, H., Kanno, M. & Taniguchi, M. (1997) *Science* 278, 1623–6.

Emoto, M., Emoto, Y. & Kaufmann, S. H. (1997) *Eur. J. Immunol.* 27, 183–188.

Emoto, Y., Emoto, M. & Kaufmann, S. H. (1997) *Inf. & Imm.* 65, 5003–5009.

Enomoto, A., Nishimura, H. & Yoshikai, Y. (1997) *J. Immunol.* 158, 2268–2277.

Flesch, I. E. A., Wandersee, A. & Kaufmann, S. H. E. (1997) *J. Immunol.* 159, 7–10.

Hammond, K. J. L., Poulton, L. D., Palmisano, L. J., Silveira, P. A., Godfrey, D. I. & Baxter, A. G. (1998) *J. Exp. Med.* 187, 1047–1056.

Kawano, T., Cui, J., Koezuka, Y., Toura, I., Kaneko, Y., Motoki, K., Ueno, H., Nakagawa, R., Sato, H., Kondo, E., Koseki, H. & Taniguchi, M. (1997) *Science* 278, 1626–1629.

Kawano, T., Cui, J., Koezuka, Y., Toura, I., Kaneko, Y., Sato, H., Kondo, E., Harada, M., Koseki, H., Nakayama, T., Tanaka, Y. & Taniguchi, M. (1998) *Proc. Natl. Acad. Sci. USA* 95, 5690–5693.

Koller, B. H., Marrack, P., Kappler, J. W. & Smithies, O. (1990) *Science* 248, 1227–1230.

Koseki, H., Asano, H., Inaba, T., Miyashita, N., Moriwaki, K., Lindahl, K. F., Mizutani, Y., Imai, K. & Taniguchi, M. (1991) *Proc. Natl. Acad. Sci. U.S.A.* 88, 7518–7522.

Lantz, O. & Bendelac, A. (1994) *J. Exp. Med.* 180, 1097–1106.

Levraud, J. P., Pannetier, C., Langlade-Demoyen, P., Brichard, V. & Kourilsky, P. (1996) *J. Exp. Med.* 183, 439–449.

Mieza, M. A., Itoh, T., Cui, J. Q., Makino, Y., Kawano, T., Tsuchida, K., Koike, T., Shirai, T., Yagita, H., Matsuzawa, A., Koseki, H. & Taniguchi, M. (1996) *J. Immunol.* 156, 4035–4040.

Ortaldo, J. R., Winckler-Pickett, R., Mason, A. T. & Mason, L. H. (1998) *J. Immunol.* 160, 1158–1165.

Pannetier, C., Levraud, J.-P., Lim, A., Even, J. & Kourilsky, P. (1997) in: *The T-cell receptor: selected protocols and applications.* Okseznberg, J. R., Wang, L. and Jeffery, J.-Y. Y., Eds. (Chapman and Hall, New York), pp. 287–324.

Regnault, A., Levraud, J. P., Lim, A., Six, A., Moreau, C., Cumano, A. & Kourilsky, P. (1996) *Eur. J. Immunol.* 26, 914–921.

Schofield, L., McConville, M. J., Hansen, D., Campbell, A. S., Fraser-Reid, B., Grusby, M. J. & Tachado, S. D. (1999) *Science* 283, 225–229.

Takeda, K., Seki, S., Ogasawara, K., Anzai, R., Hashimoto, W., Sugiura, K., Takahashi, M., Satoh, M. & Kumagai, K. (1996) *J. Immunol.* 156, 3366–3373.

Watanabe, H., Miyaji, C., Kawachi, Y., Liai, T., Ohtsuka, K., Iwanage, T., Takahashi-Iwanaga, H. & Abo, T. (1995) *J. Immunol.* 155, 2972–2983.

Wilson, S. B., Kent, S. C., Patton, K. T., Orban, T., Jackson, R. A., Exley, M., Porcelli, S., Schatz, D. A., Atkinson, M. A., Balk, S. P., Strominger, J. L. & Hafler, D. A. (1998) *Nature* 391, 177–181.

---

The invention claimed is:

1. A method for activating NKT cells ex vivo, comprising:
   (i) providing a biological sample containing NKT cells;
   (ii) bringing the NKT cells into contact with at least one phosphatidylinositol mannoside (PIM), under suitable conditions for the PIM to activate the NKT cells.

2. The method as claimed in claim 1, in which said PIM is of mycobacterial origin.

3. The method as claimed in either of claim 1 or 2, in which said PIM comprises 4, 5, or 6 mannose units.

\* \* \* \* \*

UNITED STATES PATENT AND TRADEMARK OFFICE
CERTIFICATE OF CORRECTION

PATENT NO. : 7,052,909 B1  Page 1 of 1
APPLICATION NO. : 09/959098
DATED : May 30, 2006
INVENTOR(S) : Irina Apostolou et al.

It is certified that error appears in the above-identified patent and that said Letters Patent is hereby corrected as shown below:

On the title page, item (12), line 2, "Apostolov" should read --Apostolou--.

On the title page, item (75), line 1, "Apostolov, Paris" should read --Apostolou, Montreuil--.

In claim 3, column 22, line 57, "claim" should read --claims--.

Signed and Sealed this

Fifth Day of September, 2006

JON W. DUDAS
*Director of the United States Patent and Trademark Office*